United States Patent
Li et al.

(10) Patent No.: US 11,760,922 B2
(45) Date of Patent: Sep. 19, 2023

(54) METHODS OF MAKING HYDRAULIC FRACTURING FLUIDS AND USE THEREOF

(71) Applicants: Saudi Arabian Oil Company, Dhahran (SA); Alfaisal University, Riyadh (SA)

(72) Inventors: Wengang Li, Khobar (SA); Edreese Alsharaeh, Riyadh (SA); Mohammed Abdullah Bataweel, Dhahran (SA)

(73) Assignees: Saudi Arabian Oil Company, Dhahran (SA); Alfaisal University, Riyadh (SA)

( * ) Notice: Subject to any disclaimer, the term of this patent is extended or adjusted under 35 U.S.C. 154(b) by 0 days.

(21) Appl. No.: 17/472,867

(22) Filed: Sep. 13, 2021

(65) Prior Publication Data
US 2021/0403799 A1    Dec. 30, 2021

Related U.S. Application Data

(60) Provisional application No. 63/078,452, filed on Sep. 15, 2020.

(51) Int. Cl.
*C09K 8/68* (2006.01)
*C09K 8/80* (2006.01)
(Continued)

(52) U.S. Cl.
CPC ........... *C09K 8/685* (2013.01); *B01J 19/0046* (2013.01); *B82Y 30/00* (2013.01); *C12M 21/08* (2013.01);
(Continued)

(58) Field of Classification Search
CPC .......... C09K 8/685; C09K 8/80; C09K 8/805; Y10S 507/903; Y10S 507/922; Y10S 507/924
See application file for complete search history.

(56) References Cited

U.S. PATENT DOCUMENTS 5,422,183 A * 6/1995 Sinclair .................... C09K 8/62
428/407
9,638,834 B2   5/2017 Jiang et al.
(Continued)

FOREIGN PATENT DOCUMENTS

CA   2933969 C    9/2015
EP   2047061 B1   3/2014
(Continued)

OTHER PUBLICATIONS

MO-67 material safety data sheet by Halliburton (Year: 2011).*
(Continued)

*Primary Examiner* — Aiqun Li
(74) *Attorney, Agent, or Firm* — DINSMORE & SHOHL LLP (57) ABSTRACT

Methods of preparing a crosslinked hydraulic fracturing fluid include combining a hydraulic fracturing fluid comprising a polyacrylamide polymer with a plurality of coated proppants. The plurality of coated proppants include a proppant particle and a resin proppant coating on the proppant particle. The resin proppant coating includes resin and a zirconium oxide crosslinker. The resin includes at least one of phenol, furan, epoxy, urethane, phenol-formaldehyde, polyester, vinyl ester, and urea aldehyde. Methods further include allowing the zirconium oxide crosslinker within the resin proppant coating to crosslink the polyacrylamide polymer within the hydraulic fracturing fluid at a pH of at least 10, thereby forming the crosslinked hydraulic fracturing fluid.

15 Claims, 1 Drawing Sheet

(51) Int. Cl.
*G01N 33/50* (2006.01)
*B82Y 30/00* (2011.01)
*B01J 19/00* (2006.01)
*C12M 3/00* (2006.01)
*C12M 1/34* (2006.01)
*C12M 1/32* (2006.01)
*C40B 60/14* (2006.01)
*B33Y 80/00* (2015.01)
*B33Y 10/00* (2015.01)

(52) U.S. Cl.
CPC ............ *C12M 23/12* (2013.01); *C12M 41/46* (2013.01); *G01N 33/502* (2013.01); *G01N 33/5008* (2013.01); *G01N 33/5058* (2013.01); *G01N 33/5064* (2013.01); *G01N 33/5073* (2013.01); *B01J 2219/0072* (2013.01); *B01J 2219/00286* (2013.01); *B01J 2219/00308* (2013.01); *B01J 2219/00313* (2013.01); *B01J 2219/00317* (2013.01); *B01J 2219/00319* (2013.01); *B01J 2219/00351* (2013.01); *B01J 2219/00376* (2013.01); *B01J 2219/00416* (2013.01); *B01J 2219/00585* (2013.01); *B01J 2219/00659* (2013.01); *B33Y 10/00* (2014.12); *B33Y 80/00* (2014.12); *C40B 60/14* (2013.01); *G01N 33/5038* (2013.01)

(56) References Cited

U.S. PATENT DOCUMENTS

| | | |
|---|---|---|
| 2012/0227967 A1 | 9/2012 | Shaikh et al. |
| 2016/0340575 A1* | 11/2016 | Nguyen .................. E21B 43/26 |
| 2018/0327657 A1* | 11/2018 | Pitchumani .............. C09K 8/66 |
| 2018/0346799 A1* | 12/2018 | Zha ....................... C08B 15/005 |
| 2019/0161673 A1 | 5/2019 | McDaniel et al. |

FOREIGN PATENT DOCUMENTS

| | | |
|---|---|---|
| WO | 2013188413 A1 | 12/2013 |
| WO | 2014182534 A1 | 11/2014 |

OTHER PUBLICATIONS

Ochi et al., "Preparation of epoxy/zirconia hybrid materials via in situ polymerization using zirconium alkoxide coordinated with acid anhydride", Materials Chemistry and Physics, vol. 129, pp. 424-432, 2011.

Search Report and Written Opinion pertaining to Application No. PCT/US2021/050017 dated Dec. 20, 2021.

* cited by examiner

METHODS OF MAKING HYDRAULIC FRACTURING FLUIDS AND USE THEREOF

CROSS-REFERENCE TO RELATED APPLICATIONS

This application claims the benefit of U.S. Provisional Application Ser. No. 63/078,452, filed Sep. 15, 2020.

TECHNICAL FIELD

Embodiments of the present disclosure generally relate to methods of making hydraulic fracturing fluids and use thereof.

BACKGROUND

Hydraulic fracturing is a stimulation treatment routinely performed on oil and gas wells. Hydraulic fracturing fluids are pumped into the subsurface formation to be treated, causing fractures to open in the subsurface formation. The wings of the fracture extend away from the wellbore in opposing directions according to the natural stresses within the formation. Proppant, such as grains of sand of a particular size, may be mixed with the treatment fluid to keep the fracture open when the treatment is complete.

SUMMARY

It is often desirable during and after fracturing a subsurface formation to hold the fractures open through the use of proppants for more effective oil and gas production than without. However, sand particles, which are used as a proppant, may not provide sufficient crush resistance for use in a given subsurface formation due to the polycrystalline nature of the grains. Conventional uncoated proppants break under downhole stress. Ceramic proppants break down in wet conditions, which cause them to lose their crush resistance. Temperatures downhole exacerbate this effect.

Proppant coatings are used to protect the proppant particle from degradation by the presence of aqueous fluids at downhole temperatures. The proppant coating increases the surface area of the particle; therefore, the crush stress is distributed over a larger area of the coated proppant particle. In turn, the distribution of force along a larger area should result in a decrease in the amount of crushed proppant particles, also known as 'the crush percentage.' The proppant coating also adheres to the proppant and prevents proppants that are crushed upon application of formation stress from releasing proppant fines. Proppant fines may migrate into the formation and restrict flow conductivity of the formation. However, coated proppants have a greater density than conventional uncoated proppants.

Conventional hydraulic fracturing fluids that suspend solid materials, such as proppants, encounter difficulties as the solids separate from the liquid and settle in the wellbore. This phenomenon is commonly referred to as "sag." Sag typically occurs when the flow of hydraulic fracturing fluid through the wellbore is stopped for a period of time, during which the hydraulic fracturing fluid is static. Sag may also occur due to decreased flow or annular velocity of the hydraulic fracturing fluid. Sag may also be worsened due to coated proppants having a density greater than uncoated proppants. Settling of the solid material may cause variations in the density of hydraulic fracturing fluid throughout the wellbore. For example, the hydraulic fracturing fluid in the bottom of the wellbore may have a greater density due to settling of the solids towards the bottom of the wellbore caused by gravity. Likewise, the hydraulic fracturing fluid near the surface may have a lesser density. Sag conditions may lead to reductions in the ability of a hydraulic fracturing fluid to prop open fractures with proppants.

Conventional hydraulic fracturing fluids require crosslinker to be added to the conventional hydraulic fracturing fluid to increase the viscosity of the conventional hydraulic fracturing fluid in order to carry coated proppants into the subsurface formation. Adding additional crosslinker to the hydraulic fracturing fluid decreases operation efficiency.

Accordingly, a need exists for hydraulic fracturing fluids and methods of making hydraulic fracturing fluids that have an increased viscosity without additional additives. Increased viscosity increases the ability of the hydraulic fracturing fluid to suspend coated proppants. The crosslinked hydraulic fracturing fluids of the present disclosure address this need by adding zirconium oxide crosslinker to the proppant coating of the plurality of proppants added to the hydraulic fracturing fluid. The zirconium oxide crosslinker present in the proppant coating crosslinks the polyacrylamide polymer presents in the hydraulic fracturing fluid, thereby increasing the viscosity of crosslinked hydraulic fracturing fluid as compared to the viscosity of the hydraulic fracturing fluid before crosslinking.

According to the subject matter of the present disclosure, a method of preparing a crosslinked hydraulic fracturing fluid is disclosed. The method includes combining a hydraulic fracturing fluid comprising a polyacrylamide polymer with a plurality of coated proppants wherein: the plurality of coated proppants comprise a proppant particle and a resin proppant coating on the proppant particle, the resin proppant coating comprising resin and a zirconium oxide crosslinker, wherein the resin comprises at least one of phenol, furan, epoxy, urethane, phenol-formaldehyde, polyester, vinyl ester, and urea aldehyde; and allowing the zirconium oxide crosslinker within the resin proppant coating to crosslink the polyacrylamide polymer within the hydraulic fracturing fluid at a pH of at least 10, thereby forming the crosslinked hydraulic fracturing fluid.

In accordance with another embodiment of the present disclosure, a method for increasing a rate of hydrocarbon production from a subsurface formation, the method comprising: producing a first rate of production of hydrocarbons from the subsurface formation through a wellbore; introducing the crosslinked hydraulic fracturing fluid into the subsurface formation; and increasing hydrocarbon production from the subsurface formation by producing a second rate of production of hydrocarbons from the subsurface formation, wherein the second rate of production of hydrocarbons is greater than the first rate of production of hydrocarbons.

Additional features and advantages of the described embodiments will be set forth in the detailed description which follows, and in part will be readily apparent to those skilled in the art from that description or recognized by practicing the described embodiments, including the detailed description which follows, the claims, as well as the drawings.

BRIEF DESCRIPTION OF THE DRAWING

The following detailed description of specific embodiments of the present disclosure can be best understood when read in conjunction with the following drawing, where like structure is indicated with like reference numerals and wherein.

DETAILED DESCRIPTION

As used throughout this disclosure, the term "condensate" refers to a liquid hydrocarbon phase that generally occurs in association with natural gas. Its presence as a liquid phase depends on temperature and pressure conditions in the reservoir allowing condensation of liquid from vapor. The production of condensate reservoirs can be complicated, because of the pressure sensitivity of some condensates. During production, there is a risk of the condensate changing from gas to liquid if the reservoir pressure decreases to less than the dew point during production. Hydrocarbon gas produced in association with condensate is called wet gas. The API gravity of condensate is typically from 50° to 120°.

As used throughout this disclosure, the term "condensate banking" refers to a relative permeability effect where condensate drops out of the vapor phase around the wellbore when the pressure decreases to less than the dew point in response to drawdown or depletion. Gas production rate may be hindered by the permeability reduction.

As used throughout this disclosure, the term "hierarchical roughness" refers to micro roughness covered with nano roughness. This differs from unitary roughness as the material is not solely micro roughness or nano roughness, but a combination of the two.

As used throughout this disclosure, the term "hydraulic fracturing" refers to a stimulation treatment routinely performed on hydrocarbon wells in reservoirs with a permeability of less than 10 milliDarcys. Hydraulic fracturing fluids are pumped into a subsurface formation, causing a fracture to form or open. The wings of the fracture extend away from the wellbore in opposing directions according to the natural stresses within the subsurface formation. Proppants are mixed with the treatment fluid to keep the fracture open when the treatment is complete. Hydraulic fracturing creates fluid communication with a subsurface formation and bypasses damage, such as condensate banking, that may exist in the near-wellbore area.

As used throughout this disclosure, the term "subsurface formation" refers to a body of rock that is sufficiently distinctive and continuous from the surrounding rock bodies that the body of rock can be mapped as a distinct entity. A subsurface formation is, therefore, sufficiently homogenous to form a single identifiable unit containing similar rheological properties throughout the subsurface formation, including, but not limited to, porosity and permeability. A subsurface formation is the fundamental unit of lithostratigraphy.

As used throughout this disclosure, the term "lithostatic pressure" refers to the pressure of the weight of overburden, or overlying rock, on a subsurface formation.

As used throughout this disclosure, the term "producing subsurface formation" refers to the subsurface formation from which hydrocarbons are produced.

As used throughout this disclosure, the term "proppants" refers to particles mixed with hydraulic fracturing fluid to hold fractures open after a hydraulic fracturing treatment. Proppant materials are carefully sorted for mesh size, roundness and sphericity to provide an efficient conduit for fluid production from the reservoir to the wellbore.

As used throughout this disclosure, the term "reservoir" refers to a subsurface formation having sufficient porosity and permeability to store and transmit fluids.

As used throughout this disclosure, the term "wings" refers to the two cracks formed by a fracture being 180° apart and typically similar in shape and size.

As used throughout this disclosure, the term "wellbore" refers to the drilled hole or borehole, including the openhole or uncased portion of the well. Borehole may refer to the inside diameter of the wellbore wall, the rock face that bounds the drilled hole.

To produce hydrocarbons from a hydrocarbon-containing reservoir, production wells are drilled to a depth that enables hydrocarbons to travel from the subsurface formation to the surface. However, when producing hydrocarbon gas, the wellbore and subsurface formation pressure decrease as the volume of hydrocarbon gas in the reservoir decreases. If pressure decreases to less than the dew point of the hydrocarbon gas, condensate may form and create a liquid blockage. This liquid blockage decreases the permeability between the wellbore and the subsurface formation thereby decreasing the rate of production of the hydrocarbon gas.

The present disclosure is directed to compositions and methods for producing crosslinked hydraulic fracturing fluids including a plurality of proppants, and to methods for increasing a rate of hydrocarbon production from a subsurface formation through the use of crosslinked hydraulic fracturing fluids including a plurality of proppants.

The crosslinked hydraulic fracturing fluid may include a plurality of proppants and a crosslinked gel. The zirconium oxide crosslinker present in the resin proppant coating that coats the plurality of proppants crosslinks the polyacrylamide polymer, guar gum, hydroxypropyl guar gum, or combinations thereof to form the crosslinked gel. Various amounts are contemplated for the crosslinked gel. In one or more embodiments, the crosslinked hydraulic fracturing fluid may include from 1 to 90 wt. %, from 1 to 80 wt. %, from 1 to 75 wt. %, from 1 to 70 wt. %, from 1 to 60 wt. %, from 1 to 50 wt. %, from 1 to 40 wt. %, from 1 to 30 wt. %, from 1 to 25 wt. %, from 1 to 20 wt. %, from 1 to 10 wt. %, from 1 to 5 wt. %, from 5 to 90 wt. %, from 5 to 80 wt. %, from 5 to 75 wt. %, from 5 to 70 wt. %, from 5 to 60 wt. %, from 5 to 50 wt. %, from 5 to 40 wt. %, from 5 to 30 wt. %, from 5 to 25 wt. %, from 5 to 20 wt. %, from 5 to 10 wt. %, from 10 to 90 wt. %, from 10 to 80 wt. %, from 10 to 75 wt. %, from 10 to 70 wt. %, from 10 to 60 wt. %, from 10 to 50 wt. %, from 10 to 40 wt. %, from 10 to 30 wt. %, from 10 to 25 wt. %, from 10 to 20 wt. %, from 20 to 90 wt. %, from 20 to 80 wt. %, from 20 to 75 wt. %, from 20 to 70 wt. %, from 20 to 60 wt. %, from 20 to 50 wt. %, from 20 to 40 wt. %, from 20 to 30 wt. %, from 20 to 25 wt. %, from 25 to 90 wt. %, from 25 to 80 wt. %, from 25 to 75 wt. %, from 25 to 70 wt. %, from 25 to 60 wt. %, from 25 to 50 wt. %, from 25 to 40 wt. %, from 25 to 30 wt. %, from 30 to 90 wt. %, from 30 to 80 wt. %, from 30 to 75 wt. %, from 30 to 70 wt. %, from 30 to 60 wt. %, from 30 to 50 wt. %, from 30 to 40 wt. %, from 40 to 90 wt. %, from 40 to 80 wt. %, from 40 to 75 wt. %, from 40 to 70 wt. %, from 40 to 60 wt. %, from 40 to 50 wt. %, from 50 to 90 wt. %, from 50 to 80 wt. %, from 50 to 75 wt. %, from 50 to 70 wt. %, from 50 to 60 wt. %, from 60 to 90 wt. %, from 60 to 80 wt. %, from 60 to 75 wt. %, from 60 to 70 wt. %, from 70 to 90 wt. %, from 70 to 80 wt. %, from 70 to 75 wt. %, from 75 to 90 wt. %, from 75 to 80 wt. %, or from 80 to 90 wt. % crosslinked gel by weight of the crosslinked hydraulic fracturing fluid.

The crosslinked gel may include a polyacrylamide polymer, guar gum, hydroxypropyl guar gum, or combinations thereof crosslinked by the zirconium oxide crosslinker. In one or more embodiments, the polyacrylamide polymer or copolymer may comprise a polyacrylamide copolymer, a polyacrylamide terpolymer, or combinations thereof. The polyacrylamide polymer, whether a copolymer, or terpolymer, may include at least one monomer selected from the group consisting of acrylic acid, or other monomers containing carboxyl groups or their salts or esters such as acrylates, and combinations thereof. Examples of said acrylates include methyl acrylate, ethyl acrylate, n-propyl acrylate, isopropyl acrylate, n-butyl acrylate, isobutyl acrylate, tert-butyl acrylate, n-octyl acrylate, and the like. Other monomers besides the carboxyl-containing monomer may include acrylamide, methacrylamide, N-substituted acrylamides. Further examples of said N-substituted acrylamides include, among others, N-methyl acrylamide, N-propyl acrylamide, N-butyl acrylamide, N,N-dimethyl acrylamide, N-methyl-N-sec-butyl acrylamide. In other embodiments, the carboxyl-containing synthetic polymer may be a partially hydrolyzed carboxyl-containing synthetic polymer.

The crosslinked hydraulic fracturing fluid may include an aqueous fluid. The aqueous fluid may include at least one of fresh water, salt water, brine, municipal water, formation water, produced water, well water, filtered water, distilled water, sea water, or combinations of these. The brine may include at least one of natural and synthetic brine, such as saturated brine or formate brine. The aqueous fluid may use water containing organic compounds or salt. Without being bound by any particular theory, salt or other organic compounds may be incorporated into the aqueous fluid to control the density of the crosslinked hydraulic fracturing fluid. Increasing the saturation of the aqueous fluid by increasing the salt concentration or the level of other organic compounds in the aqueous fluid may increase the density of the crosslinked hydraulic fracturing fluid. Suitable salts include but are not limited to alkali metal chlorides, hydroxides, or carboxylates. In some embodiments, suitable salts may include sodium, calcium, cesium, zinc, aluminum, magnesium, potassium, strontium, silicon, lithium, chlorides, bromides, carbonates, iodides, chlorates, bromates, formates, nitrates, sulfates, phosphates, oxides, fluorides and combinations of these. In some particular embodiments, brine may be used in the aqueous fluid. Without being bound by any particular theory, brine may be used to create osmotic balance between the crosslinked hydraulic fracturing fluid and the subterranean formation.

In some embodiments, the crosslinked hydraulic fracturing fluid may include from 1 to 90 wt. %, from 1 to 80 wt. %, from 1 to 75 wt. %, from 1 to 70 wt. %, from 1 to 60 wt. %, from 1 to 50 wt. %, from 1 to 40 wt. %, from 1 to 30 wt. %, from 1 to 25 wt. %, from 1 to 20 wt. %, from 1 to 10 wt. %, from 1 to 5 wt. %, from 5 to 90 wt. %, from 5 to 80 wt. %, from 5 to 75 wt. %, from 5 to 70 wt. %, from 5 to 60 wt. %, from 5 to 50 wt. %, from 5 to 40 wt. %, from 5 to 30 wt. %, from 5 to 25 wt. %, from 5 to 20 wt. %, from 5 to 10 wt. %, from 10 to 90 wt. %, from 10 to 80 wt. %, from 10 to 75 wt. %, from 10 to 70 wt. %, from 10 to 60 wt. %, from 10 to 50 wt. %, from 10 to 40 wt. %, from 10 to 30 wt. %, from 10 to 25 wt. %, from 10 to 20 wt. %, from 20 to 90 wt. %, from 20 to 80 wt. %, from 20 to 75 wt. %, from 20 to 70 wt. %, from 20 to 60 wt. %, from 20 to 50 wt. %, from 20 to 40 wt. %, from 20 to 30 wt. %, from 20 to 25 wt. %, from 25 to 90 wt. %, from 25 to 80 wt. %, from 25 to 75 wt. %, from 25 to 70 wt. %, from 25 to 60 wt. %, from 25 to 50 wt. %, from 25 to 40 wt. %, from 25 to 30 wt. %, from 30 to 90 wt. %, from 30 to 80 wt. %, from 30 to 75 wt. %, from 30 to 70 wt. %, from 30 to 60 wt. %, from 30 to 50 wt. %, from 30 to 40 wt. %, from 40 to 90 wt. %, from 40 to 80 wt. %, from 40 to 75 wt. %, from 40 to 70 wt. %, from 40 to 60 wt. %, from 40 to 50 wt. %, from 50 to 90 wt. %, from 50 to 80 wt. %, from 50 to 75 wt. %, from 50 to 70 wt. %, from 50 to 60 wt. %, from 60 to 90 wt. %, from 60 to 80 wt. %, from 60 to 75 wt. %, from 60 to 70 wt. %, from 70 to 90 wt. %, from 70 to 80 wt. %, from 70 to 75 wt. %, from 75 to 90 wt. %, from 75 to 80 wt. %, or from 80 to 90 wt. % of the aqueous fluid based on the total weight of the crosslinked hydraulic fracturing fluid.

In embodiments, the crosslinked hydraulic fracturing fluid may include a pH adjuster, such as NaOH, KOH, RbOH, $NH_3$, or combinations thereof. The crosslinked hydraulic fracturing fluid may have a pH of at least 9, at least 10, at least 10.5, at least 11, at least 11.5, at least 12, at least 12.5, at least 13, or at least 13.5. The crosslinked hydraulic fracturing fluid may have a pH of from 9 to 14, from 9 to 13.5, from 9 to 13, from 9 to 12.5, from 9 to 12, from 9 to 11.5, from 9 to 11, from 9 to 10.5, from 10 to 14, from 10 to 13.5, from 10 to 13, from 10 to 12.5, from 10 to 12, from 10 to 11.5, from 10 to 11, from 10 to 10.5, from 10.5 to 14, from 10.5 to 13.5, from 10.5 to 13, from 10.5 to 12.5, from 10.5 to 12, from 10.5 to 11.5, from 10.5 to 11, from 11 to 14, from 11 to 13.5, from 11 to 13, from 11 to 12.5, from 11 to 12, from 11 to 11.5, from 11.5 to 14, from 11.5 to 13.5, from 11.5 to 13, from 11.5 to 12.5, from 11.5 to 12, from 12 to 14, from 12 to 13.5, from 12 to 13, from 12 to 12.5, from 12.5 to 14, from 12.5 to 13.5, from 12.5 to 13, from 13 to 14, from 13 to 13.5, or from 13.5 to 14. The pH adjuster may adjust the pH of the fluid to be within any of the ranges described.

The crosslinked hydraulic fracturing fluid may also include additional additives, for example, additives that alter the salt concentration of the crosslinked gel. In one or more embodiments, brine solution may be added, such as KCl or $CaCl_2$).

Optionally, the crosslinked hydraulic fracturing fluid may also include additional components such as buffers, antioxidants, biocides, clay stabilizers, diverting agents, fluid loss additives, friction reducers, iron controllers, gel stabilizers, etc. The crosslinked hydraulic fracturing fluid may further include a surfactant, which may be used to lower the surface tension of the crosslinked hydraulic fracturing fluid.

Various surfactants are contemplated, for example, anionic surfactants, cationic surfactants, amphoteric surfactants, zwitterionic surfactants, or combinations thereof. Non-limiting examples of anionic surfactants include sulfonated polymers, sulfonated alkanes, polycarboxylated ethers, or combinations of these. Non-limiting examples of cationic surfactants include trimethylalkylammonium salts, alkylbenxylammonium salts, or combinations of these. Non-limiting examples of neutral surfactants include proteins, polyethylene glycol derivatives, oligosaccharides, cholesterol derivatives, or combinations of these. The surfactant may include at least one of sulfonated polymers, sulfonated alkanes, polycarboxylated ethers, trimethylalkylammonium salts, alkylbenzylammonium salts, proteins, polyethylene glycol derivatives, oligosaccharides, or cholesterol derivatives. The crosslinked hydraulic fracturing fluid fluid may contain from 0.01 wt. % to 20 wt. % of the surfactant based on the total weight of the crosslinked hydraulic fracturing fluid fluid. The crosslinked hydraulic fracturing fluid fluid may contain from 0.02 lb/bbl to 180 lb/bbl of the surfactant based on the total weight of the crosslinked hydraulic fracturing fluid fluid, such as from 0.02 to 150 lb/bbl, or from 0.05 to 150 lb/bbl. In some embodiments, the crosslinked hydraulic fracturing fluid fluid may contain from 0.1 to 150 lb/bbl, or from 0.1 to 100 lb/bbl, or from 1 to 100 lb/bbl of the surfactant.

Optionally, the crosslinked hydraulic fracturing fluid may also include a breaker to degrade the crosslinked gel. The breaker is used to "break" or reduce the viscosity of the crosslinked hydraulic fracturing fluid so that the crosslinked hydraulic fracturing fluid may be easily recovered from the fracture during clean up. In one or more embodiments, the breaker may be an acid, an oxidizer, an enzyme breaker, a chelating agent, or a combination thereof. Examples of breakers include, but are not be limited to sodium bromate, potassium bromate, sodium persulfate, ammonium persulfate, potassium persulfate, and various peroxides. Additionally, an encapsulant may be used to control or delay the release of the breaker encapsulated or disposed therein. In one or more embodiments, the breaker may include a combination of encapsulated and unencapsulated breaker. For example, the breaker may include a combination of sodium bromate and encapsulated sodium bromate.

As previously stated, the crosslinked hydraulic fracturing fluid may include a plurality of proppants. The plurality of proppants may include proppant particles and a resin proppant coating. The resin proppant coating includes resin and a zirconium oxide crosslinker. The resin proppant coating coats the proppant particle. The resin proppant coating may be of uniform thickness or may include changes in thickness throughout, leading to hierarchical roughness in the resin proppant coating. The hierarchical roughness of the resin coating may range from 5 nm to 100 µm, from 5 nm to 50 µm, from 5 nm to 10 µm, from 5 nm to 1 µm, from 5 nm to 50 nm, from 50 nm to 100 µm, from 50 nm to 50 µm, from 50 nm to 10 µm, from 50 nm to 1 µm, from 1 µm to 100 µm, from 1 µm to 50 µm, from 1 µm to 10 µm, from 10 µm to 100 µm, from 10 µm to 50 µm, or from 50 µm to 100 µm. The resin coated proppants may be introduced into a wellbore within a hydraulic fracturing fluid. The resin coated proppants may prop open fractures within a subsurface formation, where the subsurface formation is a producing formation having a hydrocarbon reservoir. Propping open the fractures increases the rate of hydrocarbon production and the overall amount of hydrocarbon production.

Figure 1:
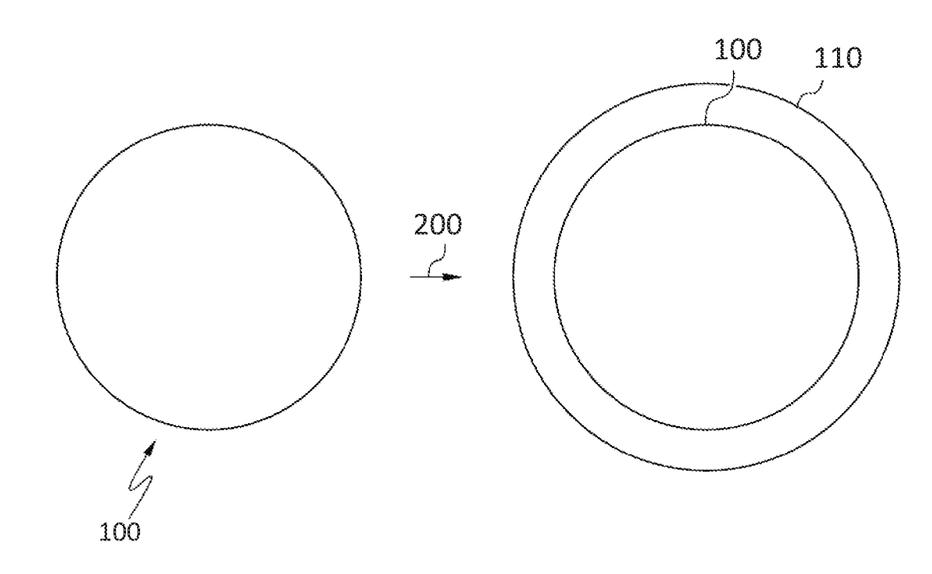
FIG. 1 is a schematic view of a proppant particle and a coated proppant, according to one or more embodiments described in this disclosure.

FIG. 1 schematically portrays two states of a proppant particle 100. On the left, a proppant particle 100 is depicted in a first, uncoated state. Then, on the right, a coated proppant is depicted wherein the proppant particle 100 is in a second, coated state. In the second state, the proppant particle 100 has undergone a coating step 200 to be coated with a resin proppant coating 110, forming a coated proppant.

The proppant particle may be chosen from any type of proppant suitable for use in hydraulic fracturing applications. As previously described, proppants are propping agent particles used in hydraulic fracturing fluids to maintain and hold open subsurface fractures during or following subsurface treatment. In some embodiments, the proppant particle may include particles of materials such as oxides, silicates, sand, ceramic, resin, epoxy, plastic, mineral, glass, or combinations thereof. For instance, the proppant particle may include graded sand, treated sand, ceramic, or plastic. The proppant particle may include particles of bauxite, sintered bauxite, $Ti^{4+}$/polymer composites, where the superscript "4+" stands for the oxidation state of titanium, titanium nitride (TiN), or titanium carbide. The proppant particle may include glass particles or glass beads. Embodiments of the present disclosure may utilize at least one proppant particle and in embodiments wherein more than one proppant particle is used, the proppant particles may contain a mixture of two or more different materials.

The material of the proppant particle may be chosen based on the particular application and characteristics desired, such as the depth of the subsurface formation wherein the proppant particles will be used, as proppant particles with greater mechanical strength are needed at greater lithostatic pressures. In embodiments, the lithostatic pressure may be from 3000 to 10,000 psi, from 3000 to 9000 psi, from 3000 to 8500 psi, from 3000 to 8000 psi, from 3000 to 7500 psi, from 3050 to 10,000 psi, from 3050 to 9000 psi, from 3050 to 8500 psi, from 3050 to 8000 psi, from 3050 to 7500 psi, from 3500 to 10,000 psi, from 3500 to 9000 psi, from 3500 to 8500 psi, from 3500 to 8000 psi, from 3500 to 7500 psi, from 4000 to 10,000 psi, from 5000 to 10,000 psi, from 6000 to 10,000 psi, from 7000 to 10,000 psi, or any combination thereof. For instance, ceramic proppant materials exhibit greater strength, thermal resistance, and conductivity than sands. Additionally, ceramic proppant materials have more uniform size and shape than sands. Fully (pre-cured) or partially cured (curable) unfunctionalized organic resin-coated sand may be chosen in embodiments to provide sand particles of irregular size and shape with greater crush resistance strength and conductivity.

The proppant particle may include various sizes or shapes. In some embodiments, the one or more proppant particles may have sizes from 8 mesh to 140 mesh (diameters from 105 micrometers (µm) to 2380 µm). In some embodiments, the proppant particles may have sizes from 8 mesh to 16 mesh (diam. 2380 µm to 1180 µm), 16 mesh to 30 mesh (diam. 600 µm to 1190 µm), 20 mesh to 40 mesh (diam. 420 µm to 840 µm), 30 mesh to 50 mesh (diam. 300 µm to 595 µm), 40 mesh to 70 mesh (diam. 210 µm to 420 µm) or 70 mesh to 140 mesh (diam. 105 µm to 210 µm).

In some embodiments, the proppant particles may have a rough surface texture that may increase adhesion of the resin proppant coating to the proppant particle. The surfaces of the proppant particles may be roughened to increase the surface area of the proppant particle by any suitable physical or chemical method, including, for example, using an appropriate etchant. In some embodiments, the proppant particle may have a surface that provides a desired adhesion of the resin proppant coating to the proppant particle or may already be sufficiently rough without a need for chemical or physical roughening. Specifically, ball milling proppant particles may provide relatively rounder particles as well as particles with increased surface roughness.

The term "rough" refers to a surface having at least one deviation from the normalized plane of the surface, such as a depression or protrusion. The surface may be uneven and irregular and may have one or more imperfections, such as dimples, stipples, bumps, projections or combinations of these. The rough surface may have an arithmetic average roughness ($R_a$) of greater than or equal to 1 nanometer (nm) (1 nm=0.001 µm). $R_a$ is defined as the arithmetic average of the differences between the local surface heights and the average surface height and can be described by Equation 1, contemplating n measurements:

$$R_a = \frac{1}{n}\sum_{i=1}^{n}|y_i|  \qquad \text{EQUATION 1}$$

In Equation 1, each $y_i$ is the amount of deviation from the normalized plane of the surface (meaning the depth or height of a depression or protrusion, respectively) of the absolute value of the ith of n measurements. Thus, $R_a$ is the arithmetic average of the absolute values of n measurements of deviation y from the normalized plane of the surface. In some embodiments, the surface of the proppant particle may have an $R_a$ of greater than or equal to 2 nm (0.002 µm), or greater than or equal to 10 nm (0.01 μm), or greater than or equal to 50 nm (0.05 μm), or greater than or equal to 100 nm (0.1 μm), or greater than or equal to 1 μm.

As previously discussed in this disclosure, the resin proppant coating includes a zirconium oxide ($ZrO_2$) crosslinker. In embodiments, the coated proppant includes from 0.1 to 20 wt. %, from 0.1 to 17.5 wt. %, from 0.1 to 15 wt. %, from 0.1 to 12.5 wt. %, from 0.1 to 10 wt. %, from 0.1 to 7.5 wt. %, from 0.1 to 5 wt. %, from 0.1 to 2.5 wt. %, from 0.1 to 1 wt. %, from 0.1 to 0.5 wt. %, from 0.5 to 20 wt. %, from 0.5 to 17.5 wt. %, from 0.5 to 15 wt. %, from 0.5 to 12.5 wt. %, from 0.5 to 10 wt. %, from 0.5 to 7.5 wt. %, from 0.5 to 5 wt. %, from 0.5 to 2.5 wt. %, from 0.5 to 1 wt. %, from 1 to 20 wt. %, from 1 to 17.5 wt. %, from 1 to 15 wt. %, from 1 to 12.5 wt. %, from 1 to 10 wt. %, from 1 to 7.5 wt. %, from 1 to 5 wt. %, from 1 to 2.5 wt. %, from 2.5 to 20 wt. %, from 2.5 to 17.5 wt. %, from 2.5 to 15 wt. %, from 2.5 to 12.5 wt. %, from 2.5 to 10 wt. %, from 2.5 to 7.5 wt. %, from 2.5 to 5 wt. %, from 5 to 20 wt. %, from 5 to 17.5 wt. %, from 5 to 15 wt. %, from 5 to 12.5 wt. %, from 5 to 10 wt. %, from 5 to 7.5 wt. %, from 7.5 to 20 wt. %, from 7.5 to 17.5 wt. %, from 7.5 to 15 wt. %, from 7.5 to 12.5 wt. %, from 7.5 to 10 wt. %, from 10 to 20 wt. %, from 10 to 17.5 wt. %, from 10 to 15 wt. %, from 10 to 12.5 wt. %, from 12.5 to 20 wt. %, from 12.5 to 17.5 wt. %, from 12.5 to 15 wt. %, from 15 to 20 wt. %, from 15 to 17.5 wt. %, or from 17.5 to 20 wt. % zirconium oxide crosslinker as calculated by a weight of the resin proppant coating.

As previously discussed in this disclosure, the resin proppant coating includes resin and a zirconium oxide crosslinker. Resin is a solid or viscous substance of plant or synthetic origin that is typically convertible into polymers, and may be a mixture of organic compounds such as terpenes, an organic compound produced by plants. The viscosity of resin may be greater than 20 centiPoise (cP), measured at a temperature of 120° C. In one embodiment, the resin may have no additional additives. The resin may include at least one of phenol, furan, epoxy, urethane, phenol-formaldehyde, polyester, vinyl ester, and urea aldehyde. The resin may include epoxy. The phenol-formaldehyde resin may include novolac or resole. Novolacs are phenol-formaldehyde resins with a formaldehyde to phenol molar ratio of less than 1, where the phenol units are mainly linked by methylene or ether groups, or both. The novolac polymer may have a molecular weight of from 1,000 to 100,000 grams per mole (g/mol), from 1,000 to 50,000 g/mol, from 1,000 to 25,000 g/mol, from 1,000 to 10,000 g/mol, from 1,000 to 5,000 g/mol, 5,000 to 100,000 g/mol, from 5,000 to 50,000 g/mol, from 5,000 to 25,000 g/mol, from 5,000 to 10,000 g/mol, 10,000 to 100,000 g/mol, from 10,000 to 50,000 g/mol, from 10,000 to 25,000 g/mol, from 25,000 to 50,000 g/mol, from 25,000 to 100,000 g/mol, or from 50,000 to 100,000 g/mol. The novolac polymer includes a glass transition temperature greater than 250° F., 300° F., 350° F., 390° F., 400° F., 450° F., or 500° F. Novolacs are stable, meaning that novolacs do not react and do retain their polymer properties at temperatures of up to 300° F., 400° F., 425° F., 450° F., 475° F., 500° F., 550° F., or 600° F. Resoles are phenol-formaldehyde resins with a formaldehyde to phenol molar ratio of more than 1, where the phenol units are mainly linked by methylene or ether groups, or both. This can harden without the addition of a crosslinking agent due to abundance of methylene to bridge the phenol groups. The resole may have a molecular weight of from 1,000 to 100,000 g/mol, from 1,000 to 50,000 g/mol, from 1,000 to 25,000 g/mol, from 1,000 to 10,000 g/mol, from 1,000 to 5,000 g/mol, 5,000 to 100,000 g/mol, from 5,000 to 50,000 g/mol, from 5,000 to 25,000 g/mol, from 5,000 to 10,000 g/mol, 10,000 to 100,000 g/mol, from 10,000 to 50,000 g/mol, from 10,000 to 25,000 g/mol, from 25,000 to 50,000 g/mol, from 25,000 to 100,000 g/mol, or from 50,000 to 100,000 g/mol.

The coated proppants may include from 0.5 to 20 wt. %, from 0.5 to 15 wt. %, from 0.5 to 10 wt. %, from 0.5 to 8 wt. %, from 0.5 to 6 wt. %, from 0.5 to 5 wt. %, from 0.5 to 4.5 wt. %, from 0.5 to 2 wt. %, from 0.5 to 1 wt. %, 1 to 20 wt. %, from 1 to 15 wt. %, from 1 to 10 wt. %, from 1 to 8 wt. %, from 1 to 6 wt. %, from 1 to 5 wt. %, from 1 to 4.5 wt. %, from 1 to 2 wt. %, 2 to 20 wt. %, from 2 to 15 wt. %, from 2 to 10 wt. %, from 2 to 8 wt. %, from 2 to 6 wt. %, from 2 to 5 wt. %, from 2 to 4.5 wt. %, 1 to 2 wt. %, 4.5 to 20 wt. %, from 4.5 to 15 wt. %, from 4.5 to 10 wt. %, from 4.5 to 8 wt. %, from 4.5 to 6 wt. %, from 4.5 to 5 wt. %, 5 to 20 wt. %, from 5 to 15 wt. %, from 5 to 10 wt. %, from 5 to 8 wt. %, from 5 to 6 wt. %, 8 to 20 wt. %, from 8 to 15 wt. %, from 8 to 10 wt. %, from 10 to 15 wt. %, from 10 to 20 wt. %, or from 15 to 20 wt. % resin as calculated by a weight of the proppant particles.

The coated proppants may include from 0.5 to 20 wt. %, from 0.5 to 15 wt. %, from 0.5 to 10 wt. %, from 0.5 to 8 wt. %, from 0.5 to 6 wt. %, from 0.5 to 5 wt. %, from 0.5 to 4.5 wt. %, from 0.5 to 2 wt. %, from 0.5 to 1 wt. %, 1 to 20 wt. %, from 1 to 15 wt. %, from 1 to 10 wt. %, from 1 to 8 wt. %, from 1 to 6 wt. %, from 1 to 5 wt. %, from 1 to 4.5 wt. %, from 1 to 2 wt. %, 2 to 20 wt. %, from 2 to 15 wt. %, from 2 to 10 wt. %, from 2 to 8 wt. %, from 2 to 6 wt. %, from 2 to 5 wt. %, from 2 to 4.5 wt. %, 1 to 2 wt. %, 4.5 to 20 wt. %, from 4.5 to 15 wt. %, from 4.5 to 10 wt. %, from 4.5 to 8 wt. %, from 4.5 to 6 wt. %, from 4.5 to 5 wt. %, 5 to 20 wt. %, from 5 to 15 wt. %, from 5 to 10 wt. %, from 5 to 8 wt. %, from 5 to 6 wt. %, 8 to 20 wt. %, from 8 to 15 wt. %, from 8 to 10 wt. %, from 10 to 15 wt. %, from 10 to 20 wt. %, or from 15 to 20 wt. % resin proppant coating as calculated by a weight of the proppant particles.

The resin proppant coating may further include a strengthening agent. The strengthening agent may include at least one of glass fibers, carbon fibers, Kevlar fibers, carbon nanotubes, silica, alumina, mica, nanoclay, graphene, boron nitride nanotubes, vanadium pentoxide, zinc oxide, calcium carbonate, zirconium oxide, nanosilica, nanoalumina, nanozinc oxide, nanotubes, nanocalcium carbonate, nanozirconium oxide, nanotitanic oxide, and graphene. The strengthening agent may include carbon nanotubes. Carbon nanotubes include at least one of single-walled nanotubes, double-walled nanotubes, multi-walled carbon nanotubes, or narrow-walled nanotubes. The carbon nanotubes have a diameter of from 1 to 200 nm, from 20 to 100 nm, from 10 to 80 nm, from 4 to 20 nm, from 2 to 12 nm, from 2 to 10 nm, from 2 to 9 nm, from 2 to 8 nm, from 2 to 7 nm, from 2 to 6 nm, from 2 to 5 nm, from 2 to 4 nm, from 2 to 3 nm, 3 to 12 nm, from 3 to 10 nm, from 3 to 9 nm, from 3 to 8 nm, from 3 to 7 nm, from 3 to 6 nm, from 3 to 5 nm, from 3 to 4 nm, 4 to 12 nm, from 4 to 10 nm, from 4 to 9 nm, from 4 to 8 nm, from 4 to 7 nm, from 4 to 6 nm, from 4 to 5 nm, 5 to 12 nm, from 5 to 10 nm, from 5 to 9 nm, from 5 to 8 nm, from 5 to 7 nm, from 5 to 6 nm, 6 to 12 nm, from 6 to 10 nm, from 6 to 9 nm, from 6 to 8 nm, from 6 to 7 nm, 7 to 12 nm, from 7 to 10 nm, from 7 to 9 nm, from 7 to 8 nm, 8 to 12 nm, from 8 to 10 nm, from 8 to 9 nm, 9 to 12 nm, from 9 to 10 nm, from 10 to 12 nm, or of 8 nm; a length of from 20 to 500 μm, 20 to 200 μm, 20 to 150 μm, 20 to 100 μm, 50 to 500 μm, from 50 to 200 μm, from 50 to 150 μm, from 50 to 100 μm, from 100 to 500 μm, from 100 to 200 μm, from 100 to 150 μm, from 150 to 500 μm, from 150 to 200 µm, or from 200 to 500 µm; an aspect ratio of from 100 to 50,000, from 500 to 30,000, from 1,000 to 20,000, from 1,000 to 100,000, from 1,000 to 50,000, from 1,000 to 40,000, from 1,000 to 30,000, from 1,000 to 25,000, from 1,000 to 20,000, from 1,000 to 15,000, from 1,000 to 12,000, from 1,000 to 10,000, from 1,000 to 8,000, from 8,000 to 100,000, from 8,000 to 50,000, from 8,000 to 40,000, from 8,000 to 30,000, from 8,000 to 25,000, from 8,000 to 20,000, from 8,000 to 15,000, from 8,000 to 12,000, from 8,000 to 10,000, from 10,000 to 100,000, from 10,000 to 50,000, from 10,000 to 40,000, from 10,000 to 30,000, from 10,000 to 25,000, from 10,000 to 20,000, from 10,000 to 15,000, from 10,000 to 12,000, from 12,000 to 100,000, from 12,000 to 50,000, from 12,000 to 40,000, from 12,000 to 30,000, from 12,000 to 25,000, from 12,000 to 20,000, from 12,000 to 15,000, from 15,000 to 100,000, from 15,000 to 50,000, from 15,000 to 40,000, from 15,000 to 30,000, from 15,000 to 25,000, from 15,000 to 20,000, from 20,000 to 100,000, from 20,000 to 50,000, from 20,000 to 40,000, from 20,000 to 30,000, from 20,000 to 25,000, from 25,000 to 100,000, from 25,000 to 50,000, from 25,000 to 40,000, from 25,000 to 30,000, from 30,000 to 100,000, from 30,000 to 50,000, from 30,000 to 40,000, from 40,000 to 50,000, from 40,000 to 100,000, or from 50,000 to 100,000; and a specific surface area of from 100 to 12,000 square meter per gram ($m^2$/g), from 100 to 10,000 $m^2$/g, from 100 to 800 $m^2$/g, from 100 to 700 $m^2$/g, from 400 to 12,000 $m^2$/g, from 400 to 10,000 $m^2$/g, from 400 to 800 $m^2$/g, from 100 to 1,500 $m^2$/g, from 120 to 1,000 $m^2$/g, from 150 to 850 $m^2$/g, or from 400 to 700 $m^2$/g, where the specific surface area is calculated through the Brunauer-Emmett-Teller (BET) theory. The multi-walled carbon nanotubes include a metal oxide percentage of 10 wt. % or less, 5 wt. % or less, 3 wt. % or less, 2 wt. % or less, 1.5 wt. % or less, 1 wt. % or less, or 0.5 wt. % or less; and a bulk density of from 0.001 to 0.12 grams per cubic centimeter (g/$cm^3$), from 0.01 to 0.08 g/$cm^3$, from 0.02 to 0.06 g/$cm^3$, from 0.01 to 1 g/$cm^3$, from 0.01 to 0.5 g/$cm^3$, from 0.01 to 0.2 g/$cm^3$, from 0.01 to 0.1 g/$cm^3$, from 0.01 to 0.05 g/$cm^3$, from 0.01 to 0.02 g/$cm^3$, from 0.02 to 1 g/$cm^3$, from 0.02 to 0.5 g/$cm^3$, from 0.02 to 0.2 g/$cm^3$, from 0.02 to 0.1 g/$cm^3$, from 0.02 to 0.05 g/$cm^3$, from 0.05 to 1 g/$cm^3$, from 0.05 to 0.5 g/$cm^3$, from 0.05 to 0.2 g/$cm^3$, from 0.05 to 0.1 g/$cm^3$, from 0.06 to 0.08 g/$cm^3$, from 0.1 to 1 g/$cm^3$, 0.1 to 0.5 g/$cm^3$, from 0.1 to 0.2 g/$cm^3$, from 0.2 to 1 g/$cm^3$, from 0.2 to 0.5 g/$cm^3$, or from 0.5 to 1 g/$cm^3$. The resin proppant coating may include from 1 to 15 wt. %, from 1 to 12 wt. %, from 1 to 10 wt. %, from 1 to 8 wt. %, from 1 to 5 wt. %, from 5 to 15 wt. %, from 5 to 12 wt. %, from 5 to 10 wt. %, from 5 to 8 wt. %, from 8 to 15 wt. %, from 8 to 12 wt. %, from 8 to 10 wt. %, from 10 to 15 wt. %, from 10 to 12 wt. %, or from 12 to 15 wt. % of the strengthening agent. The resin proppant coating may include less than or equal to 20 wt. %, 15 wt. %, 10 wt. %, 5 wt. %, 2 wt. %, 1.5 wt. %, 1 wt. %, 0.75 wt. %, 0.5 wt. %, 0.2 wt. %, or 0.1 wt. % of the strengthening agent. The coated proppants may include from 0.1 to 10 wt. %, from 0.1 to 5 wt. %, from 0.1 to 3 wt. %, from 0.1 to 2 wt. %, from 0.1 to 1.5 wt. %, from 0.1 to 1 wt. %, from 0.1 to 0.5 wt. %, from 0.1 to 0.2 wt. %, 0.2 to 10 wt. %, from 0.2 to 5 wt. %, from 0.2 to 3 wt. %, from 0.2 to 2 wt. %, from 0.2 to 1.5 wt. %, from 0.2 to 1 wt. %, from 0.2 to 0.5 wt. %, from 0.5 to 10 wt. %, from 0.5 to 5 wt. %, from 0.5 to 3 wt. %, from 0.5 to 2 wt. %, from 0.5 to 1.5 wt. %, from 0.5 to 1 wt. %, from 1 to 10 wt. %, from 1 to 5 wt. %, from 1 to 3 wt. %, from 1 to 2 wt. %, from 1 to 1.5 wt. %, from 1.5 to 10 wt. %, from 1.5 to 5 wt. %, from 1.5 to 3 wt. %, from 1.5 to 2 wt. %, from 2 to 10 wt. %, from 2 to 5 wt. %, from 2 to 3 wt. %, from 3 to 10 wt. %, from 3 to 5 wt. %, or from 5 to 10 wt. % strengthening agent as calculated by a weight of the resin proppant coating.

The resin proppant coating may further include a tracer material. The suitable tracer material may include, but are not limited to, ionic contrast agents such as thorium dioxide ($ThO_2$), barium sulfate ($BaSO_4$), diatrizoate, metrizoate, iothalamate, and ioxaglate; and non-ionic contrast agents such as iopamidol, iohexol, ioxilan, iopromide, iodixanol, and ioversol. Furthermore, the tracer material may be present in a range of from 0.001 to 5.0 wt. %, from 0.001 to 3 wt. %, from 0.001 to 1 wt. %, from 0.001 to 0.5 wt. %, from 0.001 to 0.1 wt. %, from 0.005 wt. %, from 0.005 to 5.0 wt. %, from 0.005 to 3 wt. %, from 0.005 to 1 wt. %, from 0.005 to 0.5 wt. %, from 0.005 to 0.1 wt. %, from 0.01 to 5.0 wt. %, from 0.01 to 3 wt. %, from 0.01 to 1 wt. %, from 0.01 to 0.5 wt. %, from 0.5 to 5.0 wt. %, from 0.5 to 3 wt. %, from 0.5 to 1 wt. %, from 1 to 5.0 wt. %, from 1 to 3 wt. %, or from 3 to 5 wt. % as calculated by a weight of the resin proppant coating.

The resin proppant coating may further include a coupling agent. A coupling agent is a compound that provides a chemical bond between two dissimilar materials, such as an inorganic material and an organic material. The coupling agent may form a bond between the proppant particle and the resin. The coupling agent may include at least one of epoxy, amino, aryl, and vinyl groups. In some embodiments, the coupling agent may include at least one of 3-glycidoxypropyltrimethoxysilane, 3-aminopropyltriethoxysilane, 3-aminopropyltrimethoxysilane, and 3-chloropropyltrimethoxysilane. The coupling agent may include from 0.1 to 20 volume percent (vol. %), from 0.1 to 15 vol. %, from 0.1 to 10 vol. %, from 0.1 to 5 vol. %, from 0.1 to 3 vol. %, from 0.1 to 1 vol. %, from 0.1 to 0.5 vol %, 0.1 to 20 vol. %, from 0.5 to 20 vol. %, from 0.5 to 15 vol. %, from 0.5 to 10 vol. %, from 0.5 to 5 vol. %, from 0.5 to 3 vol. %, from 0.5 to 1 vol. %, from 1 to 20 vol. %, from 1 to 15 vol. %, from 1 to 10 vol. %, from 1 to 5 vol. %, from 1 to 3 vol. %, from 3 to 20 vol. %, from 3 to 15 vol. %, from 3 to 10 vol. %, from 3 to 5 vol. %, from 5 to 20 vol. %, from 5 to 15 vol. %, from 5 to 10 vol. %, from 10 to 20 vol. %, from 10 to 15 vol. %, or from 15 to 20 vol. % 3-glycidoxypropyltrimethoxysilane and from 80 to 99.9 vol. %, from 80 to 99.5 vol. %, from 80 to 99 vol. %, from 80 to 95 vol. %, from 80 to 90 vol. %, from 80 to 85 vol. %, from 85 to 99.9 vol. %, from 85 to 99.5 vol. %, from 85 to 99 vol. %, from 85 to 95 vol. %, from 85 to 90 vol. %, from 90 to 99.9 vol. %, from 90 to 99.5 vol. %, from 90 to 99 vol. %, from 90 to 95 vol. %, 95 to 99.9 vol. %, from 95 to 99.5 vol. %, from 95 to 99 vol. %, from 99 to 99.9 vol. %, from 99 to 99.5 vol. %, from 99 to 99.9 vol. %, or from 99.5 to 99.9 vol. % deionized water. The resin proppant coating may include from 0.001 to 20 wt. %, from 0.001 to 15 wt. %, from 0.001 to 10 wt. %, from 0.001 to 5 wt. %, from 0.001 to 2 wt. %, from 0.001 to 1 wt. %, from 0.001 to 0.2 wt. %, from 0.001 to 0.05 wt. %, from 0.05 to 20 wt. %, from 0.05 to 15 wt. %, from 0.05 to 10 wt. %, from 0.05 to 5 wt. %, from 0.05 to 2 wt. %, from 0.05 to 1 wt. %, from 0.05 to 0.2 wt. %, from 0.2 to 20 wt. %, from 0.2 to 15 wt. %, from 0.2 to 10 wt. %, from 0.2 to 5 wt. %, from 0.2 to 2 wt. %, from 0.2 to 1 wt. %, from 1 to 20 wt. %, from 1 to 15 wt. %, from 1 to 10 wt. %, from 1 to 5 wt. %, from 1 to 2 wt. %, from 2 to 20 wt. %, from 2 to 15 wt. %, from 2 to 10 wt. %, from 2 to 5 wt. %, from 5 to 20 wt. %, from 5 to 15 wt. %, from 5 to 10 wt. %, from 10 to 20 wt. %, from 10 to 15 wt. %, or from 15 to 20 wt. % coupling agent as calculated by a weight of the resin proppant coating.

The resin proppant coating may further include an additional crosslinker. A crosslinker is a substance or agent that induces the subsurface formation of crosslinks. Mixing an unpolymerized or partially polymerized resin with a crosslinker results in a chemical reaction that crosslinks the resin. A crosslinked resin proppant coating may retain its shape without dissolving in the hydraulic fracturing fluid, while maintaining a sufficient attraction or bond to the proppant particle. The degree of crosslinking may be controlled by the molar or weight ratio of crosslinker to monomer. In some embodiments, the crosslinker may include at least one of hexamethylenetetramine, paraformaldehyde, oxazolidines, melamine resins, aldehyde donors, or resole polymers. The coated proppants may include from 8 to 20 wt. %, from 8 to 18 wt. %, from 8 to 15 wt. %, from 10 to 20 wt. %, from 10 to 18 wt. %, from 10 to 16 wt. %, from 10 to 15 wt. %, from 13 to 20 wt. %, from 13 to 18 wt. %, or from 13 to 15 wt. % additional crosslinker as calculated by a weight of the resin proppant coating.

In some embodiments, the resin proppant coating further includes a lubricating agent to reduce friction on the resin proppant coating. The lubricating agent may include at least one of calcium stearate or silicone oil. The resin proppant coating may include from 0.01 to 8 wt. %, from 0.01 to 3.75 wt. %, from 0.01 to 1.75 wt. %, from 0.25 to 8 wt. %, from 0.25 to 3.75 wt. %, from 0.25 to 1.75 wt. %, from 0.75 to 8 wt. %, from 0.75 to 3.75 wt. %, or from 0.75 to 1.75 wt. % lubricating agent as calculated by a weight of the resin proppant coating.

The resin proppant coating may further include an accelerating agent. The accelerating agent may include at least one of hydrochloric acid, Lewis acid, boron trifluoride etherate, zinc or manganese ions, acetic acid, carboxylic acid, sodium hydroxide, or salts, such as zinc acetate. The resin proppant coating may include from 1 to 70 wt. %, from 1 to 45 wt. %, from 1 to 20 wt. %, from 5 to 70 wt. %, from 5 to 45 wt. %, from 5 to 12 wt. %, from 12 to 70 wt. %, from 12 to 45 wt. %, from 12 to 20 wt. % accelerating agent as calculated by a weight of the proppant particles.

Referring again to FIG. 1, in one or more embodiments, the proppant particle 100 may be coated with a resin proppant coating 110 during a coating step 200 to produce, form, or result in a coated proppant. In some embodiments, the resin proppant coating 110 may be a surface layer on or bound to the proppant particle 100. Such a surface layer may coat at least a portion of the surface of the proppant particle 100. The resin proppant coating 110 may coat the entire surface of the proppant particle 100 (as shown) or, alternatively, may only partially surround the proppant particle 100 (not shown), leaving at least a portion of surface of the proppant particle 100 uncoated or otherwise exposed. Also not shown, the resin proppant coating 110 may be the outermost coating of the proppant particle with one or more other intervening coatings positioned between the resin proppant coating 110 and the proppant particle 100. This means that in such an embodiment the resin proppant coating 110 is coupled to the proppant particle 100 as opposed to contacting the proppant particle 100 as shown in FIG. 1.

Further embodiments of the present disclosure are directed to methods of preparing a crosslinked hydraulic fracturing fluid. The methods may include combining a hydraulic fracturing fluid including a polyacrylamide polymer with a plurality of coated proppants. The plurality of coated proppants and the crosslinked hydraulic fracturing fluid may include any of the embodiments previously described in this disclosure.

The hydraulic fracturing fluid may be similar to the crosslinked hydraulic fracturing fluid as previously described in this disclosure, but without the crosslinked gel as previously described. The hydraulic fracturing fluid may include an aqueous fluid as previously described. The hydraulic fracturing fluid may also include additional additives, as previously described.

The hydraulic fracturing fluid may include from 0.1 to 2 wt. %, from 0.1 to 1.5 wt. %, from 0.1 to 1 wt. %, from 0.1 to 0.5 wt. %, from 0.5 to 2 wt. %, from 0.5 to 1.5 wt. %, from 0.5 to 1 wt. %, from 1 to 2 wt. %, from 1 to 1.5 wt. %, or from 1.5 to 2 wt. % polyacrylamide polymer by weight of the hydraulic fracturing fluid. In one or more embodiments, the polyacrylamide polymer or copolymer may comprise a polyacrylamide copolymer, a polyacrylamide terpolymer, or combinations thereof. The polyacrylamide polymer, whether a copolymer, or terpolymer, may include at least one monomer selected from the group consisting of acrylic acid, or other monomers containing carboxyl groups or their salts or esters such as acrylates, and combinations thereof. Examples of said acrylates include methyl acrylate, ethyl acrylate, n-propyl acrylate, isopropyl acrylate, n-butyl acrylate, isobutyl acrylate, tert-butyl acrylate, n-octyl acrylate, and the like. Other monomers besides the carboxyl-containing monomer may include acrylamide, methacrylamide, N-substituted acrylamides. Further examples of said N-substituted acrylamides include, among others, N-methyl acrylamide, N-propyl acrylamide, N-butyl acrylamide, N,N-dimethyl acrylamide, N-methyl-N-sec-butyl acrylamide. In other embodiments, the carboxyl-containing synthetic polymer may be a partially hydrolyzed carboxyl-containing synthetic polymer.

The methods may further include allowing the zirconium oxide crosslinker within the resin proppant coating to crosslink the polyacrylamide polymer within the hydraulic fracturing fluid at a pH of at least 10, thereby forming the crosslinked hydraulic fracturing fluid. In embodiments, allowing the zirconium oxide crosslinker to crosslink the polyacrylamide polymer bonds the plurality of coated proppants to the crosslinked hydraulic fracturing fluid. In embodiments, the zirconium oxide crosslinker may promote crosslinking between the polyacrylamide polymer present in the hydraulic fracturing fluid, thereby forming three-dimensional polymer networks. In embodiments, the plurality of proppants may be dispersed within the three-dimensional polymer networks. In embodiments, the three-dimensional polymer network may be the crosslinked gel previously described. In embodiments, allowing the zirconium oxide crosslinker to crosslink the polyacrylamide polymer bonds the plurality of coated proppants to the crosslinked hydraulic fracturing fluid, thereby forming the crosslinked gel as previously described.

In embodiments, allowing the zirconium oxide crosslinker to crosslink the polyacrylamide polymer increases the viscosity of the crosslinked hydraulic fracturing fluid as compared to the hydraulic fracturing fluid. The viscosity may be increased by at least 100 cP, by at least 90 cP, by at least 80 cP, by at least 75 cP, by at least 70 cP, by at least 65 cP, by at least 60 cP, by at least 55 cP, by at least 50 cP, by at least 40 cP, by at least 30 cP, or by at least 20 cP. In embodiments, the viscosity may increase by from 20 to 100 cP, from 30 to 100 cP, from 40 to 100 cP, from 50 to 100 cP, from 60 to 100 cP, from 65 to 100 cP, from 70 to 100 cP, from 75 to 100 cP, from 80 to 100 cP, from 20 to 90 cP, from 30 to 90 cP, from 40 to 90 cP, from 50 to 90 cP, from 60 to 90 cP, from 65 to 90 cP, from 70 to 90 cP, from 75 to 90 cP, from 80 to 90 cP, from 20 to 85 cP, from 30 to 85 cP, from 40 to 85 cP, from 50 to 85 cP, from 60 to 85 cP, from 65 to 85 cP, from 70 to 85 cP, from 75 to 85 cP, from 80 to 85 cP, from 20 to 82 cP, from 30 to 82 cP, from 40 to 82 cP, from 50 to 82 cP, from 60 to 82 cP, from 65 to 82 cP, from 70 to 82 cP, from 75 to 82 cP, from 80 to 82 cP, from 20 to 80 cP, from 30 to 80 cP, from 40 to 80 cP, from 50 to 80 cP, from 60 to 80 cP, from 65 to 80 cP, from 70 to 80 cP, from 75 to 80 cP, from 20 to 75 cP, from 30 to 75 cP, from 40 to 75 cP, from 50 to 75 cP, from 60 to 75 cP, from 65 to 75 cP, from 70 to 75 cP, from 20 to 70 cP, from 30 to 70 cP, from 40 to 70 cP, from 50 to 70 cP, from 60 to 70 cP, from 65 to 70 cP, from 20 to 65 cP, from 30 to 65 cP, from 40 to 65 cP, from 50 to 65 cP, from 60 to 65 cP, from 20 to 60 cP, from 30 to 60 cP, from 40 to 60 cP, from 50 to 60 cP, from 20 to 50 cP, from 30 to 50 cP, from 40 to 50 cP, from 20 to 40 cP, from 30 to 40 cP, from 20 to 30 cP, or approximately 82 cP. In embodiments, the viscosity of the hydraulic fracturing fluid may be from 80 to 189 cP, from 80 to 150 cP, from 80 to 130 cP, from 80 to 120 cP, from 80 to 110 cP, from 90 to 189 cP, from 90 to 150 cP, from 90 to 130 cP, from 90 to 120 cP, from 90 to 110 cP, from 100 to 189 cP, from 100 to 150 cP, from 100 to 130 cP, from 100 to 120 cP, from 100 to 110 cP, from 105 to 189 cP, from 105 to 150 cP, from 105 to 130 cP, from 105 to 120 cP, from 105 to 110 cP, or approximately 108 cP. In embodiments, the viscosity of the crosslinked hydraulic fracturing fluid may be from 110 to 230 cP, from 110 to 210 cP, from 110 to 200 cP, from 110 to 195 cP, from 130 to 230 cP, from 130 to 210 cP, from 130 to 200 cP, from 130 to 195 cP, from 150 to 230 cP, from 150 to 210 cP, from 150 to 200 cP, from 150 to 195 cP, from 170 to 230 cP, from 170 to 210 cP, from 170 to 200 cP, from 170 to 195 cP, from 180 to 230 cP, from 180 to 210 cP, from 180 to 200 cP, from 180 to 195 cP, from 185 to 230 cP, from 185 to 210 cP, from 185 to 200 cP, from 185 to 195 cP, or approximately 190 cP.

The method may further include adding a pH adjuster to the hydraulic fracturing fluid. The pH adjuster may include NaOH. In embodiments, allowing the zirconium oxide crosslinker to crosslink the polyacrylamide polymer includes increasing the pH of the hydraulic fracturing fluid from 8. Similarly, adding the pH adjuster may result in increasing the pH of the hydraulic fracturing fluid to at least 10, at least 10.5, at least 11, at least 11.5, at least 12, at least 12.5, at least 13, or at least 13.5. In embodiments, adding the pH adjuster may result in increasing the pH of the hydraulic fracturing fluid to from 10 to 14, from 10 to 13.5, from 10 to 13, from 10 to 12.5, from 10 to 12, from 10 to 11.5, from 10 to 11, from 10 to 10.5, from 10.5 to 14, from 10.5 to 13.5, from 10.5 to 13, from 10.5 to 12.5, from 10.5 to 12, from 10.5 to 11.5, from 10.5 to 11, from 11 to 14, from 11 to 13.5, from 11 to 13, from 11 to 12.5, from 11 to 12, from 11 to 11.5, from 11.5 to 14, from 11.5 to 13.5, from 11.5 to 13, from 11.5 to 12.5, from 11.5 to 12, from 12 to 14, from 12 to 13.5, from 12 to 13, from 12 to 12.5, from 12.5 to 14, from 12.5 to 13.5, from 12.5 to 13, from 13 to 14, from 13 to 13.5, or from 13.5 to 14.

Further embodiments of the present disclosure are directed to methods for producing coated proppants with a resin proppant coating. The method includes forming the resin proppant coating by mixing the resin with the zirconium oxide crosslinker. The method further includes coating proppant particles with the resin proppant coating to produce coated proppants with crosslinked resin proppant coating.

In some embodiments, the zirconium oxide crosslinker and resin may be uniformly distributed throughout the coating. The method for producing coated proppants may include coating the proppant particles using a two-layer coating or multi-layered coating system. The method may include coating the proppant particles with the resin, and then coating the proppant particles with the zirconium oxide crosslinker. In another embodiment, the proppant particles may be coated with the zirconium oxide crosslinker prior to coating the proppant particles with the resin proppant coating. These layers may be of uniform thickness or may include changes in thickness throughout, leading to hierarchical roughness in the resin proppant coating. In some embodiments, the method may further include melting the resin prior to the coating step, in the case of a solid resin, such as novolac.

Coating the proppant particles may include mixing the proppant particles with the resin proppant coating. In other embodiments, coating the proppant particles with resin proppant coating includes coating the proppant particles with from 1 to 10 wt. % resin proppant coating as calculated by a weight of the proppant particles.

Coating the proppant particles may also further include mixing the proppant particles, the resin proppant coating, and a surfactant to prevent clumping. The surfactant may be anionic, cationic, zwitterionic, or nonionic. The anionic surfactants may include at least one of sulfate esters, sulfonate esters, phosphate esters, and carboxylates. The nonionic surfactants may include at least one of ethoxylates, fatty acid esters of polyhydroxy compounds, amine oxides, sulfoxides, and phosphine oxides. The ethoxylates may include at least one of fatty alcohol ethoxylates, alkylphenol ethoxylates, fatty acid ethoxylates, ethoxylated fatter esters, ethoxylated oils, ethoxylated amines, fatty acid amides, and terminally blocked ethoxylates. The fatty acid esters of polyhydroxy compounds may include at least one of fatty acid esters of glycerol, fatty acid esters of sorbitol, fatty acid esters of sucrose, and alkyl polyglucosides.

The method may further include coating the proppants with at least one of a lubricating agent, a resin, a coupling agent, an additional crosslinker, an accelerating agent, and a strengthening agent, in addition to the resin and the zirconium oxide crosslinker. The strengthening agent may include at least one of glass fibers, carbon fibers, Kevlar fibers, mica, silica, alumina, carbon nanotubes, nanosilica, nanoalumina, nanozinc oxide, nanotubes, nanocalcium carbonate, nanocalcium carbonate, and nanozirconium oxide. In other embodiments, the method includes coating proppant particles with a top coating. The top coating may be an overlying layer that may be added for additional properties or features. As a non-limiting example, additional coatings may be used in conjunction with, or may include, a breaker, asphaltene inhibitors, wax inhibitor, scale inhibitors, iron sulfide dissolvers, iron inhibitor, delayed acid generator, or combinations of these. As used throughout this disclosure, a "breaker" refers to a compound that may break or degrade the fracturing fluid after a fracturing operation to prevent subsurface formation damage. In some embodiments, the breaker may be an oxidizer or enzyme breaker. The breaker may be any suitable materials capable of degrading a coating material.

The method for producing coated proppants may include heating the proppant particles up to from 10° C. to 250° C., up to from 370° F. to 425° F., up to 50° F., up to 75° F., up to 100° F., up to 125° F., up to 150° F., up to 175° F., up to 200° F., up to 300° F., up to 350° F., up to 370° F., up to 400° F., up to 425° F., up to 450° F., or up to 500° F. prior to the coating step. The heating may include calcining by any suitable process such as by forced hot air heating, convection, friction, conduction, combustion, exothermic reactions, microwave heating, or infrared radiation, for example.

In some embodiments, the method may further include roughening the proppant particles before the coating step. The proppant particles may be chemically or physically roughened, as previously described.

In some embodiments, the coating step may include contacting the proppant particle with the mixture in a fluidized bed process. In some embodiments, the coating step may include a stationary, bubbling, circulation, or vibratory fluidized bed process. In some embodiments, the coating step may include spraying or saturating the proppant particles with the mixture. The coating step may include, in some embodiments, tumbling or agitating the coated proppants to prevent agglomeration or clumping. The coating step may include adding another compound to the mixture, such as a solvent, an initiator, an adhesion promoter, or an additive, to form the resin proppant coating. In some embodiments, the coating process may be conducted with an emulsion coating technique. In some embodiments, the adhesion promoter may include a silane (for example, amino silane) or a silane-containing monomer. In some embodiments, an adhesion promoter may not be necessary to coat the proppant particles.

A crosslinked hydraulic fracturing fluid and a method for increasing a rate of hydrocarbon production from a subsurface formation is also disclosed. A crosslinked hydraulic fracturing fluid may be used to propagate fractures within a subsurface formation and further open fractures. The crosslinked hydraulic fracturing fluid may be any of the embodiments disclosed in this disclosure. In embodiments, the crosslinked hydraulic fracturing fluid may include a clay-based component including one or more components selected from the group consisting of lime (CaO), $CaCO_3$, bentonite, montmorillonite clay, barium sulfate (barite), hematite ($Fe_2O_3$), mullite ($3Al_2O_3 \cdot 2SiO_2$ or $2Al_2O_3 \cdot SiO_2$), kaolin, ($Al_2Si_2O_5(OH)_4$ or kaolinite), alumina ($Al_2O_3$, or aluminum oxide), silicon carbide, tungsten carbide, or combinations thereof.

Coated proppants within the crosslinked hydraulic fracturing fluid may aid in treating subsurface fractures, to prop open and keep open the fracture. The method may include producing a first rate of production of hydrocarbons from the subsurface formation through a wellbore. Then, the method may include introducing the crosslinked hydraulic fracturing fluid of this disclosure into the subsurface formation; and increasing hydrocarbon production from the subsurface formation by producing a second rate of production of hydrocarbons from the subsurface formation, wherein the second rate of production of hydrocarbons is greater than the first rate of production of hydrocarbons.

In embodiments, the method comprises introducing the crosslinked hydraulic fracturing fluid of this disclosure into the subsurface formation; and allowing hydraulic fracturing with the crosslinked hydraulic fracturing fluid to occur in the subsurface formation to extract hydrocarbons from the subsurface formation.

The crosslinked hydraulic fracturing fluid in the subsurface fracture may include coated proppants suspended in the crosslinked hydraulic fracturing fluid. In some embodiments, the coated proppants may be distributed throughout the crosslinked hydraulic fracturing fluid. The coated proppants may not aggregate or otherwise coalesce within the subsurface formation, owing in part to the crosslinked hydraulic fracturing fluid. In embodiments, the coated proppants may not aggregate or otherwise coalesce within the subsurface formation, owing in part to the crosslinked gel. The crosslinked hydraulic fracturing fluid may be pumped into the subsurface formation or may be otherwise contacted with the subsurface formation.

Embodiments of methods of treating a subsurface formation may include propagating at least one subsurface fracture in the subsurface formation to treat the subsurface formation. In some embodiments, the subsurface formation may be a rock or shale subsurface formation. In some embodiments, contacting of the subsurface formation may include drilling into the subsurface formation and subsequently injecting the crosslinked hydraulic fracturing fluid into at least one subsurface fracture in the subsurface formation. In some embodiments, the crosslinked hydraulic fracturing fluid may be pressurized before being injected into the subsurface fracture in the subsurface formation.

EXAMPLES

The following example illustrates features of the present disclosure but is not intended to limit the scope of the disclosure.

Example 1

An example for a coating recipe for a plurality of proppants as described in this disclosure is detailed in Table 1.

TABLE 1

Steps to achieve coated proppants.

| | Coating Steps |
|---|---|
| 1 | Add 150 g of 40/70 mesh silica sand available from Delmon with a 250 mL glass beaker. |
| 2 | Put the glass beaker with the 150 g of sand atop a heating mantle at 300° F. for 30 minutes, while continuously mixing at 300 rpm |
| 3 | Add 1.5 g of the resin proppant coating (including epoxy and 0.1 wt. % (0.15 g) of the zirconium oxide crosslinker) into the sand while continuously mixing at 300 rpm. 1 wt. % of the resin proppant coating with respect to the amount of sand. |
| 4 | Remove the glass beaker from the heating mantle after the resin proppant coating coats the sand. |
| 5 | Add 0.375 g of the curing agent (diethylene triamine) with a syringe and mix at 300 rpm for 2 minutes (a resin to curing agent ratio of 4:1). |
| 6 | Add 0.1 wt. % (0.15 g) more of the zirconium oxide crosslinker and mix for 3 to 4 minutes. |
| 7 | Add 5 ml of 20° C. water to the mixture to quench the reaction. The water is added slowly to avoid sand aggregating inside the beaker. |
| 8 | Mix for several minutes until no water vapor is seen from the beaker |
| 9 | Transfer the resin coated proppants to a bronze mortar to cool down to 20° C. and break down into single grains by mechanical agitation. |

After forming the coated proppants, a crush test analysis was performed on the resin coated proppants of Example 1 and comparative uncoated sand proppants with a Wizard Auto Standard Automatic Compression Tester available from CONTROLS. The comparative uncoated sand proppants did not include the resin coating. A hydraulic load frame with a maximum stress level up to 103 MPa (15000 psi) was used to measure the stress resistance of the coated sand proppants. The size of the proppant particles was 40/70 mesh. The proppant sample was sieved using a 40 mesh sieve so that all tested proppant particles were within the specified size range of 40 mesh. Then, the proppant samples were applied specific stress ranging from 3000 psi to 12000 psi for a period of 2 min. The crushed proppant at each stress level was then sieved using the same sieve (40 mesh) to collect the remains and fine. The fine production (%) was calculated using Equation 2 below.

$$\text{Fine Production}(\%) = \frac{\text{Amount of Fine}(g)}{\text{Original weight of Proppant}(g)} \times 100 \quad \text{Equation 2}$$

The crush test analysis determined that the resin coated proppants of Example 1 first exhibited a fine powder production of greater than 10% at a stress of 7500 psi, whereas the comparative uncoated sand proppants first exhibited a fine powder production of greater than 10% at a stress of 3000 psi. Therefore, the resin coated proppants of Example 1 exhibited a much greater crush strength than the comparative uncoated sand proppants, which means the resin coated proppants of Example 1 may endure far greater pressure propping open fractures in the subsurface formation than the comparative uncoated sand proppants, thereby resulting in increased hydrocarbon production after hydraulic fracturing as compared to the comparative uncoated sand proppants.

Example 2

Example hydraulic fracturing fluids and whether or not gelation/crosslinking was achieved is shown in Table 2. Comparative Fluid 1 was an aqueous fluid with 0.5 wt. % polyacrylamide polymer. Inventive Fluid 1 was an aqueous fluid with 0.5 wt. % polyacrylamide polymer and zirconium oxide coated proppants. Inventive Fluid 2 was an aqueous fluid with 0.5 wt. % polyacrylamide polymer and resin coated proppants including zirconium oxide in the resin coating.

TABLE 2

Crosslinking or gelation of hydraulic fracturing fluids at different pHs.

|  | At a pH of 4 | At a pH of 7 | At a pH of 11 |
| --- | --- | --- | --- |
| Comparative Fluid 1 | No crosslinking/ gelation | No crosslinking/ gelation | No crosslinking/ gelation |
| Inventive Fluid 1 | No crosslinking/ gelation | No crosslinking/ gelation | Crosslinking/ gelation achieved in less than 30 seconds |
| Inventive Fluid 2 | No crosslinking/ gelation | No crosslinking/ gelation | Crosslinking/ gelation achieved in less than 30 seconds |

Increasing the pH of Inventive Fluids 1 and 2 showed that at a pH of greater than 7, the hydraulic fracturing fluid will crosslink when there is zirconium oxide crosslinker coated on the proppants.

Example 3

The rheology testing was done using an Anton Paar rheometer MCR-502 with a plate diameter of 40 mm, a working distance of 1.5 mm, and a shear rate of 40 $s^{-1}$. A series of viscosity testings were performed with Comparative Fluid 1 and Inventive Fluid 2. The pH was tuned to 10 by adding NaOH.

Without sand added to the system, the viscosity of Comparative Fluid 1 was stable at around 108 cP. When the self crosslinking proppants (the resin coated proppants including zirconium oxide in the resin coating) were added (forming Inventive Fluid 2), the viscosity was increased to 190 cP. The results showed a clear enhance of viscosity with the added self-crosslinking proppants to the polyacrylamide.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising." For the purposes of defining the present technology, the transitional phrase "consisting of" may be introduced in the claims as a closed preamble term limiting the scope of the claims to the recited components or steps and any naturally occurring impurities. For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter. The transitional phrases "consisting of" and "consisting essentially of" may be interpreted to be subsets of the open-ended transitional phrases, such as "comprising" and "including," such that any use of an open ended phrase to introduce a recitation of a series of elements, components, materials, or steps should be interpreted to also disclose recitation of the series of elements, components, materials, or steps using the closed terms "consisting of" and "consisting essentially of." For example, the recitation of a composition "comprising" components A, B, and C should be interpreted as also disclosing a composition "consisting of" components A, B, and C as well as a composition "consisting essentially of" components A, B, and C. Any quantitative value expressed in the present application may be considered to include open-ended embodiments consistent with the transitional phrases "comprising" or "including" as well as closed or partially closed embodiments consistent with the transitional phrases "consisting of" and "consisting essentially of."

As used in the Specification and appended Claims, the singular forms "a", "an", and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced.

It should be understood that any two quantitative values assigned to a property may constitute a range of that property, and all combinations of ranges formed from all stated quantitative values of a given property are contemplated in this disclosure. The subject matter of the present disclosure has been described in detail and by reference to specific embodiments. It should be understood that any detailed description of a component or feature of an embodiment does not necessarily imply that the component or feature is essential to the particular embodiment or to any other embodiment.

It should be apparent to those skilled in the art that various modifications and variations may be made to the embodiments described within without departing from the spirit and scope of the claimed subject matter. Thus, it is intended that the specification cover the modifications and variations of the various embodiments described within provided such modification and variations come within the scope of the appended claims and their equivalents. Unless otherwise stated within the application, all tests, properties, and experiments are conducted at room temperature and atmospheric pressure.

Having described the subject matter of the present disclosure in detail and by reference to specific embodiments of any of these, it is noted that the various details disclosed within should not be taken to imply that these details relate to elements that are essential components of the various embodiments described within, even in cases where a particular element is illustrated in each of the drawings that accompany the present description. Further, it should be apparent that modifications and variations are possible without departing from the scope of the present disclosure, including, but not limited to, embodiments defined in the appended claims. More specifically, although some aspects of the present disclosure are identified as particularly advantageous, it is contemplated that the present disclosure is not necessarily limited to these aspects.

What is claimed is:

1. A method of preparing a crosslinked hydraulic fracturing fluid comprising:
    combining a hydraulic fracturing fluid comprising a polyacrylamide polymer with a plurality of coated proppants wherein:
        the plurality of coated proppants comprise a proppant particle and a resin proppant coating on the proppant particle, the resin proppant coating consists of resin, a zirconium oxide crosslinker, a curing agent and water, wherein the resin comprises at least one of phenol, furan, epoxy, urethane, phenol-formaldehyde, polyester, vinyl ester, and urea aldehyde; and
    allowing the zirconium oxide crosslinker within the resin proppant coating to crosslink the polyacrylamide polymer within the hydraulic fracturing fluid at a pH of at least 9, thereby forming the crosslinked hydraulic fracturing fluid.

2. The method of claim 1, wherein allowing the zirconium oxide crosslinker to crosslink the polyacrylamide polymer bonds the plurality of coated proppants to the crosslinked hydraulic fracturing fluid.

3. The method of claim 1, wherein allowing the zirconium oxide crosslinker to crosslink the polyacrylamide polymer increases the viscosity of the crosslinked hydraulic fracturing fluid as compared to the hydraulic fracturing fluid.

4. The method of claim 1, further comprising adding a pH adjuster to the hydraulic fracturing fluid to increase the pH.

5. The method of claim 4, wherein the pH adjuster comprises NaOH, KOH, RbOH, $NH_3$, or combinations thereof.

6. The method of claim 4, wherein allowing the zirconium oxide crosslinker to crosslink the polyacrylamide polymer comprises increasing the pH of the hydraulic fracturing fluid from 8.

7. The method of claim 1, wherein the resin comprises epoxy.

8. The method of claim 1, wherein the coated proppant comprises from 1 to 10 wt. % resin proppant coating as calculated by a weight of the proppant particles.

9. The method of claim 1, wherein the coated proppant comprises from 0.1 to 20 wt. % zirconium oxide crosslinker as calculated by a weight of the resin proppant coating.

10. The method of claim 1, wherein the polyacrylamide polymer comprises monomers selected from the group consisting of acrylic acid, methyl acrylate, ethyl acrylate, n-propyl acrylate, isopropyl acrylate, n-butyl acrylate, isobutyl acrylate, tert-butyl acrylate, n-octyl acrylate, acrylamide, methacrylamide, N-methyl acrylamide, N-propyl acrylamide, N-butyl acrylamide, N,N-dimethyl acrylamide, N-methyl-N-sec-butyl acrylamide, and combinations thereof.

11. The method of claim 1, wherein the hydraulic fracturing fluid comprises an aqueous fluid selected from the group consisting of fresh water, salt water, brine, municipal water, formation water, produced water, well water, filtered water, distilled water, sea water, and combinations thereof.

12. The method of claim 1, wherein the hydraulic fracturing fluid further comprises biocides, breakers, dilute acids, corrosion inhibitors, buffers, stabilizers, diverting agents, fluid loss additives, friction reducers, iron controllers, surfactants, gel stabilizers, viscosifiers, or combinations thereof.

13. The method of claim 1, further comprising:
    forming the resin proppant coating by mixing resin with the zirconium oxide crosslinker;
    heating the proppant particles up to from 10° C. to 250° C. before coating the proppant particles; and
    coating the proppant particles with the resin proppant coating to produce the coated proppants.

14. A method for increasing a rate of hydrocarbon production from a subsurface formation, the method comprising:
    producing a first rate of production of hydrocarbons from the subsurface formation through a wellbore;
    introducing the crosslinked hydraulic fracturing fluid of claim 1 into the subsurface formation; and
    increasing hydrocarbon production from the subsurface formation by producing a second rate of production of hydrocarbons from the subsurface formation, wherein the second rate of production of hydrocarbons is greater than the first rate of production of hydrocarbons.

15. A method of hydraulic fracturing a subsurface formation, the method comprising:
    introducing the crosslinked hydraulic fracturing fluid of claim 1 into the subsurface formation; and
    allowing hydraulic fracturing with the crosslinked hydraulic fracturing fluid to occur in the subsurface formation to extract hydrocarbons from the subsurface formation.

* * * * *